(12) United States Patent
Wang et al.

(10) Patent No.: US 8,597,592 B2
(45) Date of Patent: Dec. 3, 2013

(54) MICROVALVE CONTROLLED PRECISION FLUID DISPENSING APPARATUS WITH A SELF-PURGING FEATURE AND METHOD FOR USE

(75) Inventors: Dong Wang, Beijing (CN); Kun Zou, Beijing (CN); Jing Cheng, Beijing (CN)

(73) Assignees: CapitalBio Corporation, Beijing (CN); Tsinghua University, Beijing (CN)

( * ) Notice: Subject to any disclaimer, the term of this patent is extended or adjusted under 35 U.S.C. 154(b) by 1032 days.

(21) Appl. No.: 11/991,723

(22) PCT Filed: Jan. 13, 2006

(86) PCT No.: PCT/CN2006/000055
§ 371 (c)(1),
(2), (4) Date: Jun. 24, 2009

(87) PCT Pub. No.: WO2007/028289
PCT Pub. Date: Mar. 15, 2007

(65) Prior Publication Data
US 2009/0301231 A1    Dec. 10, 2009

(30) Foreign Application Priority Data
Sep. 9, 2005   (CN) .......................... 2005 1 0102436

(51) Int. Cl.
*B01L 3/00* (2006.01)
(52) U.S. Cl.
USPC ........... 422/500; 422/501; 422/502; 422/503; 436/180; 222/251
(58) Field of Classification Search
USPC .......... 422/500–503, 63, 50; 222/23, 52, 251; 436/180
See application file for complete search history.

(56) References Cited

U.S. PATENT DOCUMENTS

| | | | | |
|---|---|---|---|---|
| 3,568,735 A | * | 3/1971 | Lancaster | 141/238 |
| 4,859,605 A | * | 8/1989 | Metzger et al. | 436/43 |
| 5,474,744 A | * | 12/1995 | Lerch | 422/510 |
| 6,829,954 B2 | * | 12/2004 | Katagi | 73/864.25 |

FOREIGN PATENT DOCUMENTS

| | | |
|---|---|---|
| CN | 1231621 | 10/1999 |
| CN | 1603009 | 4/2005 |
| EP | 1388369 | 7/2003 |
| JP | 2004325329 | 11/2004 |
| WO | WO-2006/024203 | 3/2006 |
| WO | WO-2006/045229 | 5/2006 |

OTHER PUBLICATIONS

Belaube et al., Sensors and Actuations (2004) 110:130-135.
Chinese Priority Document No. CN 200420093039.4, filed on Sep. 3, 2004 (based on International Application No. PCT/CN04/001343, International Filing Date: Nov. 23, 2004).
International Search Report for Application No. PCT/CN2006/000055, mailed on Jun. 29, 2006, 3 pages.
Streule et al., J. Assoc. for Laboratory Automation (2004) 9:300-306.

* cited by examiner

*Primary Examiner* — Jyoti Nagpaul
(74) *Attorney, Agent, or Firm* — Morrison & Foerster LLP

(57) ABSTRACT

An apparatus and methods for the precise, repeatable dispensing of small, sample fluid volumes, especially as related to the printing of microarrays for biological and/or chemical testing. A pressure tuning module meters fluid volumes for aspiration and dispensation and builds pressure for fluid dispensation, in conjunction with a microvalve that precisely controls the volume of the fluid dispensed under the built pressure. A pressure source can be switched in line to efficiently purge the apparatus of residual sample fluid. A working fluid can be optionally aspirated into the system, prior to aspirating the sample fluid, in order to maximize sample fluid recovery.

7 Claims, 5 Drawing Sheets

MICROVALVE CONTROLLED PRECISION FLUID DISPENSING APPARATUS WITH A SELF-PURGING FEATURE AND METHOD FOR USE

CROSS-REFERENCE TO RELATED APPLICATIONS

This application is the national phase of PCT application PCT/CN2006/000055 having an international filing date of Jan. 13, 2006, which claims priority from China application number 200510102436.2 filed Sep. 9, 2005. The contents of these documents are incorporated herein by reference.

TECHNICAL FIELD

The present invention relates to an apparatus and method for repeatably dispensing small, precise volumes of fluids with little wastage of sample. In particular, the present invention may be applied to the fabrication of microarrays for biological and chemical testing.

BACKGROUND ART

Biochip microarrays can be two-dimensional arrays of reference biological materials on substrates such as glass membranes or similar materials. Microarrays are fabricated by printing small volumes of solution containing the reference biological material on a substrate. Types of technologies for fabricating biochip microarrays include photolithography, contact printing with split pins, and non-contact dispensing.

When photolithography using optical masks is used, the microarrays are sometimes referred to as "chips" because the photolithographs techniques use are similar to those used in semiconductor manufacturing. Typically more than 100,000 different samples can be created on a 1.3 cm×1.3 cm substrate surface, but the technique is expensive and limited to oligonucleotide probes of twenty to thirty base sequences because the oligonucleotide probes are usually synthesized in situ on the substrate from nucleotides in solution.

Split pin contact printing is very simple and easily implemented. Volumes of reference biological materials are held within the gap of a pin with a split end by capillary action, until transferred to the substrate by contact. Split pin contact printing is one of the most popular current technologies for fabricating microarrays, however the sample volume printed for each spot depends on the physical dimensions of the split end of the pin which are difficult to control. Consequently the accuracy and reproducibility of printed sample fluid volumes are difficult to control at the nanoliter to microliter quantities typically dispensed.

Non contact dispensing techniques, in some ways similar to technology used in ink jet printers, can provide fluid delivery in highly accurate and repeatable volumes in nanoliter and microliter volumes. Furthermore, because contact between the dispenser and the substrate is not required for capillary fluid flow, as for the case of the split pin technique, printing speeds can be much faster, often up to 100 dots per second, or more. Non contact dispensing techniques include piezoelectric jet, thermal bubble jet, and microvalve control. Piezoelectric jet and thermal bubble jet sample fluid applicators, derived from inkjet printer technologies, have been adapted to biochip microarray manufacture, however equipment costs tend to be high. The microvalve dispensing technique tends to require lower equipment costs because it principally comprises a pump or similar component, a microvalve (generally solenoid operated), tubing that connects the pump and the microvalve, a nozzle, and associated tubing and connectors. The microvalve is generally proximate to the nozzle and can accurately and reproducibly control the amount of previously aspirated sample fluid that is dispensed, through the precise control of the time that the microvalve is open and the magnitude of the pressure applied on the fluid in the tubing.

The BioJet Plus™ series dispensers from the United States Company, Biodot, Inc. in Irvine Calif., are examples of dispensers based on microvalve non-contact dispensing technology. A syringe pump is used aspirate sample fluid to fill nearly all of the operative volume of the apparatus (including the syringe pump) with the sample fluid, prior to dispensation. Aspirate recovery upon dispensation is typically fifty to ninety percent, depending on process parameters and sample fluid properties, because of residual sample fluid retained by the system. Such wastage of biological sample fluid can be very costly. Also, the BioJet Plus™ series dispensers can take a long time to purge residual sample fluid when changing samples because it is difficult to expel all residual droplets and bubbles using the syringe pump before aspirating a new sample.

The SmartArrayer from Beijing Capitalbio Corporation (China Patent Application No. 200,420,093,039.4) similarly uses a pressure tuning module to aspirate and expel sample fluid, but most of the operative volume of the apparatus (including the tubing connecting the pressure tuning module and the microvalve) can be partly filled with air, in order to reduce sample wastage.

SUMMARY OF THE INVENTION

Embodiments of the present invention provide apparatus and methods for the precise, repeatable dispensing of small sample volume drops, especially as related to the fabrication of microarrays for biological and/or chemical testing. A pressure tuning module (for example: a syringe pump, adjustable bellows, or similar mechanism) meters sample volumes for aspiration and adjusts the pressure applied on the sample to be dispensed in conjunction with a microvalve that precisely controls the volume of the fluid dispensed. A pressure source, can be switched in line to efficiently purge the apparatus of residual sample. A working fluid can be optionally aspirated into the system, prior to aspirating the sample fluid, in order to minimize sample wastage.

DETAILED DESCRIPTION OF EMBODIMENTS OF THE INVENTION

Unless defined otherwise, all technical and scientific terms used herein have the same meaning as is commonly understood by one of ordinary skill in the art to which this invention belongs. All patents, applications, published applications and other publications referred to herein are incorporated by reference in their entirety. If a definition set forth in this section is contrary to or otherwise inconsistent with a definition set forth in applications, published applications and other publications that are herein incorporated by reference, the definition set forth in this section prevails over the definition that is incorporated herein by reference.

As used herein, "a" or "an" means "at least one" or "one or more."

Figure 1:
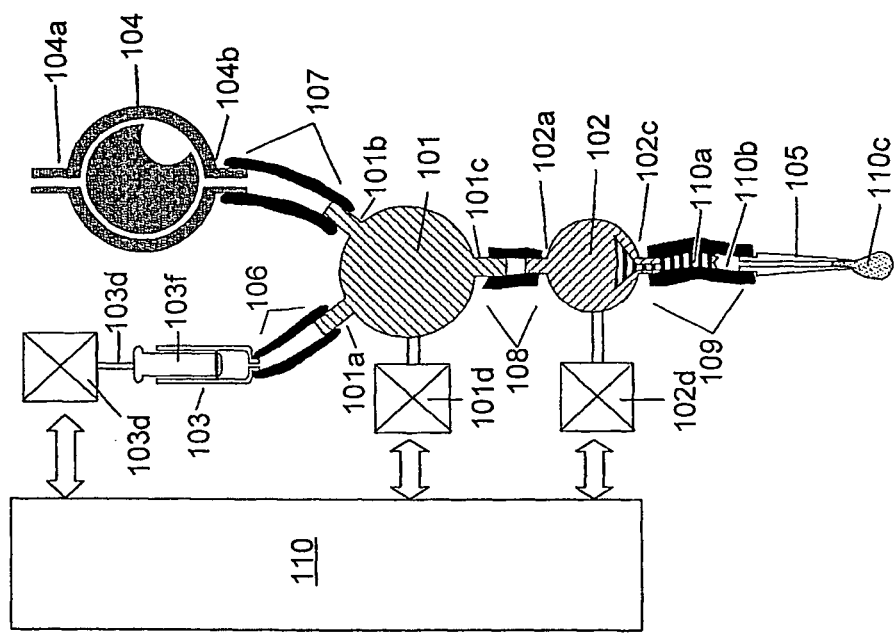
FIG. 1 is a schematic diagram of a precision fluid dispensing apparatus according to an embodiment of the invention.

FIG. 1 is a schematic diagram of an embodiment of the present invention. Nozzle 105 is used to pick up, hold, and dispense a sample fluid 110c. Nozzle 105 is connected to port 102c of microvalve 102 via coupling 109. Coupling 109 can be tubing or screw as is well known to one of ordinary skill in the art. For example, coupling 109 could be small bore Teflon® tubing. Advantageously, coupling 109 can be kept as short as possible, where mechanically feasible, in order to minimize the fluid path volume between nozzle 105 and microvalve 102 to more precisely control the dispensing of sample fluid by the microvalve 102. Microvalve 102 can be actuated to open or close by actuator 102d. In various embodiments, actuator 102d may be, for example, an electromechanical device, such as a solenoid or motor, a microelectromechanical electrical machine (MEM), or it may be pneumatically actuated using a gas or control fluid. Actuator 102d is controlled by controller 110.

Port 102a of microvalve 102 is connected to port 101c of two-way, three-port valve 101, via coupling 108. Coupling 108 can be similar to coupling 109, although it can be of larger diameter, and its length is not as significant. Two-way, three-port valve 101 can operatively connect common port 101c with either port 101a or port 101b, under the actuation of actuator 101d. Actuator 101d can be similar to actuator 102d, and operates under the control of controller 110. In some embodiments actuator 101d may additionally be manually actuated. Two-way, three-port valve 101 is actuated to connect port 101c to port 101a, that is coupled via coupling 106 to pressure tuning module 103 during sample fluid aspiration and dispensing. (In the illustrated embodiment, pressure tuning module 103 is shown as a syringe pump. Alternatively, pressure tuning module 103 could be a bellows pump, a piston pump, or a comparable mechanism. Although the use of a syringe pump is described in the following exemplary embodiments, alternate mechanisms that can be actuated to provide controlled pressures can be substituted for a syringe pump in alternate embodiments.) Two-way, three-port valve 101 is actuated to connect port 101c to port 101b that is coupled via coupling 107 to pressure source 104 during fluid purge operations.

Syringe pump 103 is actuated by actuator 103d under the control of controller 110 to aspirate and/or expel a controlled volume of the air, gas, or working fluid of the fluid paths of the apparatus, and adjust the pressure applied on the sample to be dispensed. Actuator 103d is typically electromechanical, and is coupled to the piston 103 of syringe pump 103 via a mechanical coupling 103e. Examples of actuator 103d can include stepper motors and various servo motors, coupled with gears and/or a worm drive for precise control of the position of piston 103f within syringe pump 103. In some embodiments, actuator 103d may also include motion and motion limit sensors for feedback to controller 110 for improved precision of control.

In various embodiments, pressure source 104 can be an air compressor, a compressed gas cylinder, or a pressurized reservoir of working fluid. In the case of an air compressor, an air filter and/or a pressure-relief valve may also be included between ports 101b and 104b.

Figure 2:
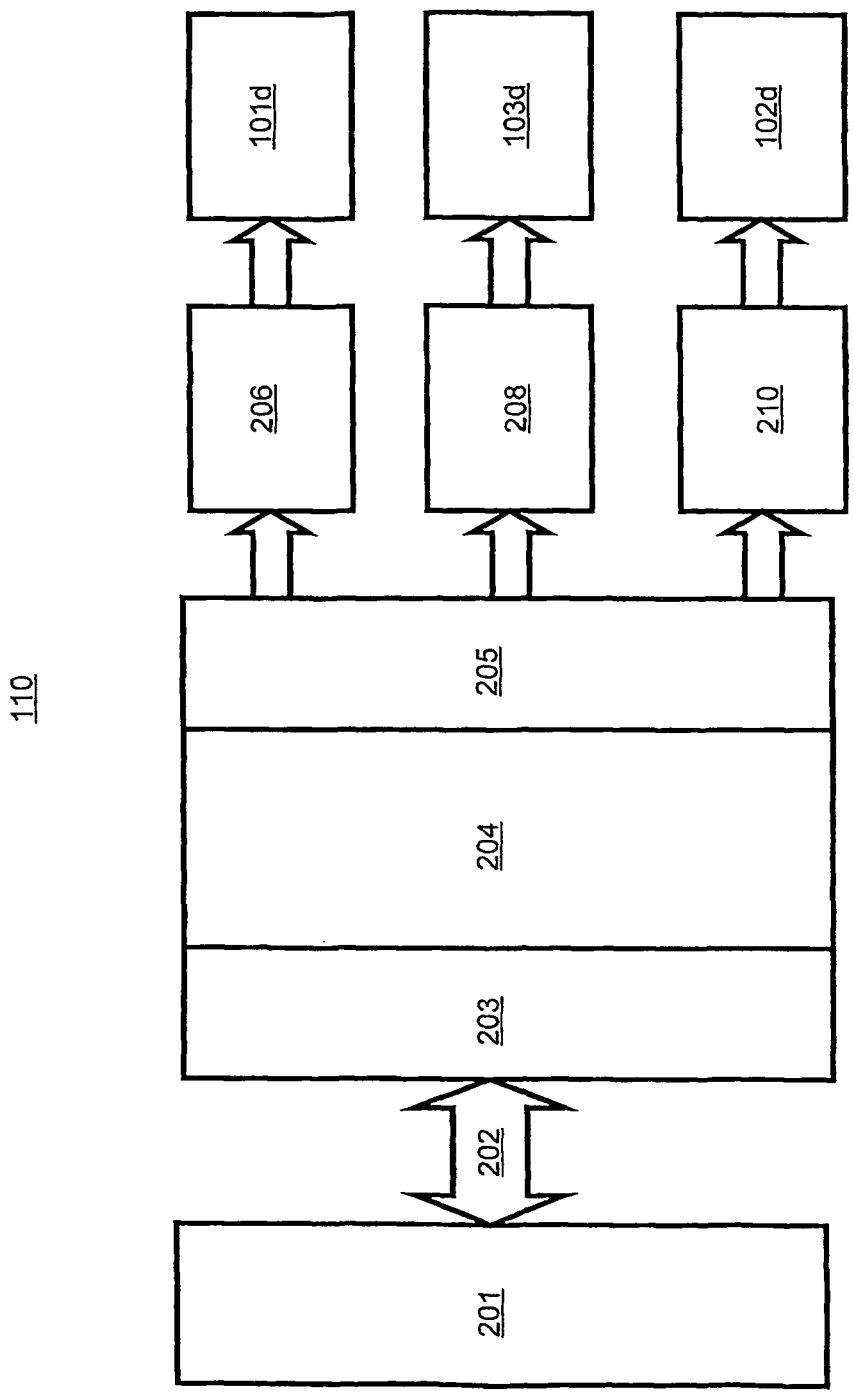
FIG. 2 is a block diagram of a control system of a precision fluid dispensing apparatus according to another embodiment of the invention.

FIG. 2 is a block diagram of a controller for an embodiment of the invention. Embedded microcontroller 204 comprises, for example, an 80C552 8-bit microprocessor from Philips Semiconductor with associated memory (not shown). Embedded microcontroller 204 communicates with actuator drive circuits 206, 208, and 210 via microcomputer I/O and expansion circuit 205. Comparable, suitable alternative embodiments are readily identified by one of ordinary skill in the embedded microcontroller arts. Actuator driver circuit 208 controls actuator 103d for the syringe pump 103. Actuator driver circuit 206 controls actuator 101d for the two-way, three port valve 101. Actuator driver circuit 210 controls actuator 102d for microvalve 102. Embedded microcontroller 204 communicates with a system operator via a personal computer 201 through serial communication port 202 and RS232 unit 203. Software controlling the fluid dispensing apparatus can execute on embedded microcontroller 204, personal computer 201, or both. A system operator selects program parameters for the operation of the fluid dispensing apparatus via a user interface on personal computer 201. In some embodiments, embedded microcontroller 204 may have rudimentary user interface features such as pushbutton controls, and/or status indicator displays.

Figure 3:
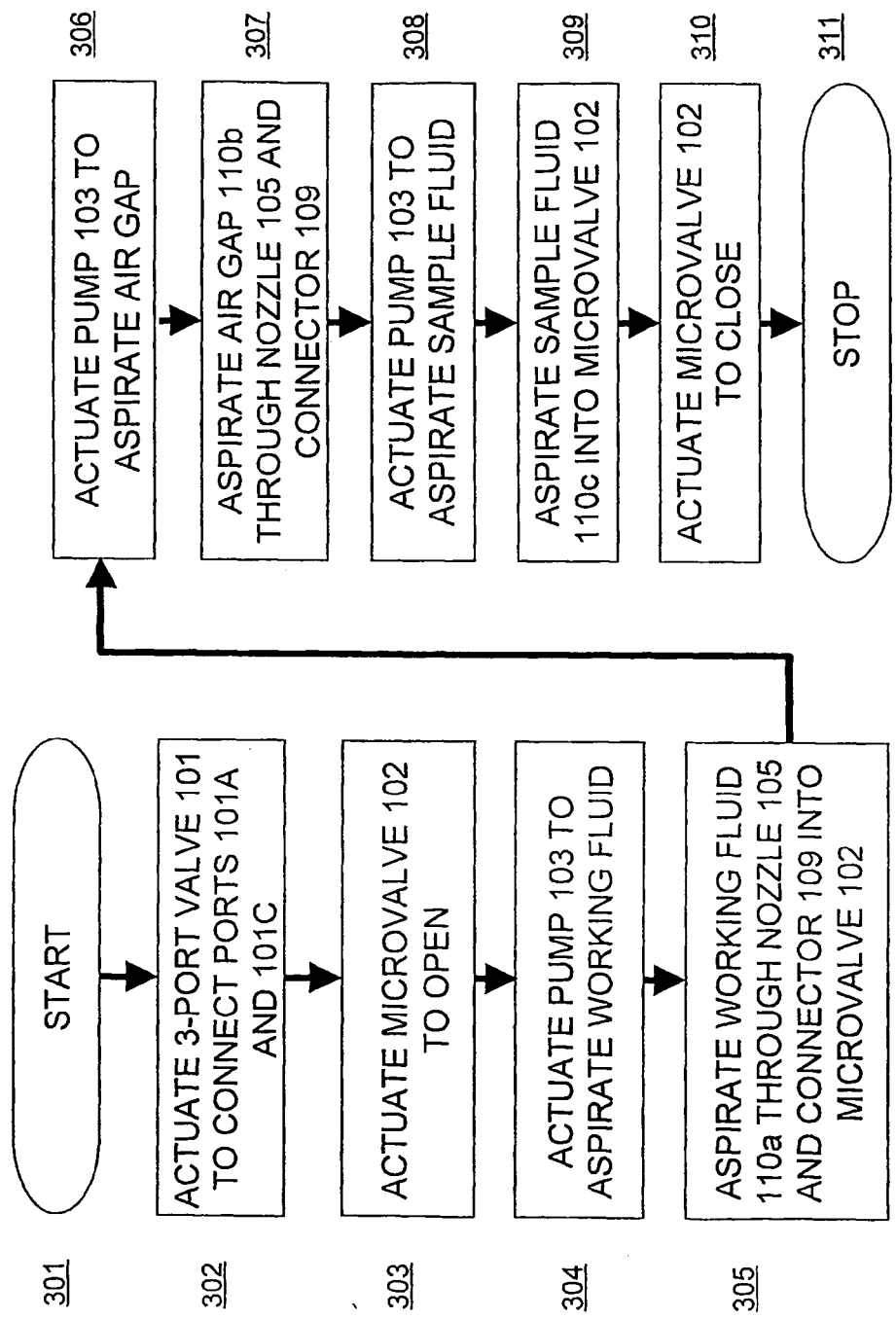
FIG. 3 is a flowchart of a method for aspirating sample fluid according to another embodiment of the invention.

FIG. 3 is a block diagram of a method embodying the filling of the invention with sample fluid. At the starting step of 301 of the sample fluid filling operation, the three port valve 101 is actuated (step 302) to connect ports 101a and 101c. Microvalve 102 is actuated to open, and syringe pump 103 is actuated to aspirate (step 304). As syringe pump 103, three-port valve 101, microvalve 102, and nozzle 105 are all in pressure and/or fluid communication in the apparatus configuration as described (see FIG. 1), the aspiration of syringe pump 103 causes whatever fluid that nozzle 105 may be dipped in to be drawn up into nozzle 105. The fluid can either be the sample fluid, directly, or it may be a working fluid to pre-fill the apparatus to enhance the recovery of sample fluid when dispensed. In the example of FIG. 3, a working fluid is first aspirated in step 305. Next, the nozzle is withdrawn from the working fluid reservoir and held in the air. In steps 306 and 307, a small amount of air (or other appropriate gas or liquid) is aspirated through nozzle 105 to separate the working fluid from the sample fluid to be aspirated next. The nozzle is then dipped in a sample fluid reservoir and in steps 308 and 309 sample fluid 110 drawn into the nozzle 105. Microvalve 102 is actuated to close in step 310.

The working fluid can be water, buffer solution, or any other sacrificial solution or solvent (preferably of lower cost than the sample fluid). Microvalve 102 operates better if it is at least partially filled with the sample fluid, or a working fluid. If an adequately large quantity of sample fluid is to be dispensed, perhaps in multiple, successive dispensing operations, the actual sample fluid can be drawn up into microvalve 102, while the residual sample fluid may be expelled to sample fluid reservoir and reused after dispensation. If a smaller quantity of sample fluid is available or required, a working fluid (110a in FIG. 1) may be drawn up into microvalve 102, followed by a small air gap 110b, and then the sample fluid 110c may be drawn. Air gap 110b keeps the sample fluid and the working fluid from mixing. The volume of sample fluid 110c that is aspirated is enough to subsequently dispense an adequate volume, but not so much extra that sample fluid is greatly wasted.

Working fluid may be optionally used to fill much more of the precision fluid dispensing apparatus, including all the way to and including syringe pump 103. To the extent that the working fluid is less compressible than air or gas alternatives that could be used to fill the combined working volume of the apparatus, transient volume differences between the volume of syringe pump 103 and nozzle 105 can be minimized during fluid aspiration or expulsion. At least the working fluid should at least partly fill the microvalve 102 because the microvalve 12 can work properly only under a certain volume of liquid filled in it.

Figure 4:
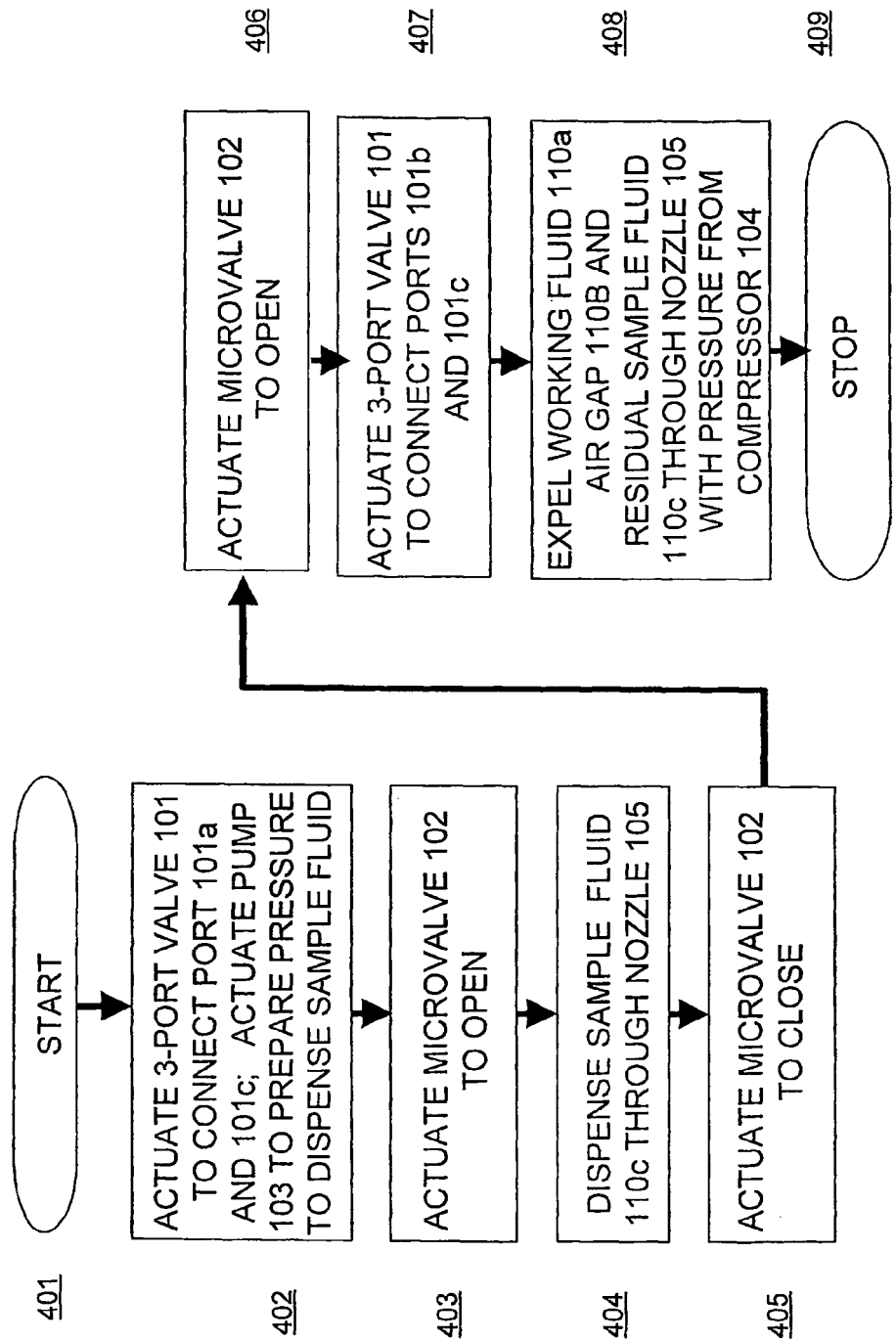
FIG. 4 is a flowchart of a method for dispensing and purging sample fluid according to another embodiment of the invention.

FIG. 4 is a block diagram of a method for dispensing sample fluid from, and purging residual fluid from an embodiment of the precision fluid dispensing apparatus. At starting step 401, it is assumed that an adequate volume of sample fluid (110c of FIG. 1) has already been aspirated into nozzle 105. It is also assumed that the nozzle 105 is now above a portion of a microarray substrate onto which the fluid sample is to be dispensed. Syringe pump 103 is actuated (step 402) to reduce the volume contained therein, thereby building pressure to expel the sample fluid. In step 403, microvalve 102 is actuated to communicate pressure between syringe pump 103 and sample nozzle 105 to expel sample fluid 110c under the pressure provided by the syringe pump 103. The magnitude of the pressure is adjustable. In step 405, microvalve 102 is actuated to close thereby terminating the dispensing of sample fluid. Other than the provided pressure, the precise time interval that microvalve 102 is actuated to be open provides the precise control of the volume of sample fluid that is dispensed. The volume change of syringe pump 103 during sample fluid aspiration and expulsion serves to set an approximate volume of sample fluid to be dispensed, thereby reducing the waste of non-dispensed sample fluid being retained in the apparatus.

Step 406 of FIG. 4 begins the operation of a residual fluid purge operation. It is assumed that the nozzle 105 is moved away from the microarray substrate work piece and placed over a waste fluid receptacle. Microvalve 102 is actuated to open in step 406 and two-way, three-port valve 101 is actuated in step 407 to connect ports 101b and 101c, thereby allowing pressure from pressure source 104 to expel (step 408) any remaining sample fluid and (if used) work fluid from the apparatus through nozzle 105 and into the waste fluid receptacle.

In other embodiments, after step 406, the two-way, three port valve 101 can be left connecting ports 101a and 101c. Nozzle 105 can be placed in a wash fluid receptacle, and syringe pump 103 can be cycled to aspirate and expel wash fluid through nozzle 105. This may then be optionally followed by steps 407 through 408 of FIG. 4 for a subsequent high pressure purge.

Referring again to FIG. 1, for the robotic fabrication of microarrays, nozzle 105, can be fixed onto the up-and-down Z axis slide of a robotic positioning device, along with microvalve 102, microvalve actuator 102d and coupler 109. The other components 101 of the embodiment of FIG. 1 can be positioned in a convenient proximity that does not interfere with the operation of the robotic position device, and coupled via coupler 108 to microvalve 102. The operation of controller 110 can be coordinated with the operation of the robotic positioning device to synchronize the dipping and positioning of nozzle 105 with associated aspiration, dispensing, and purging operations such as described in the methods, above.

Figure 5:
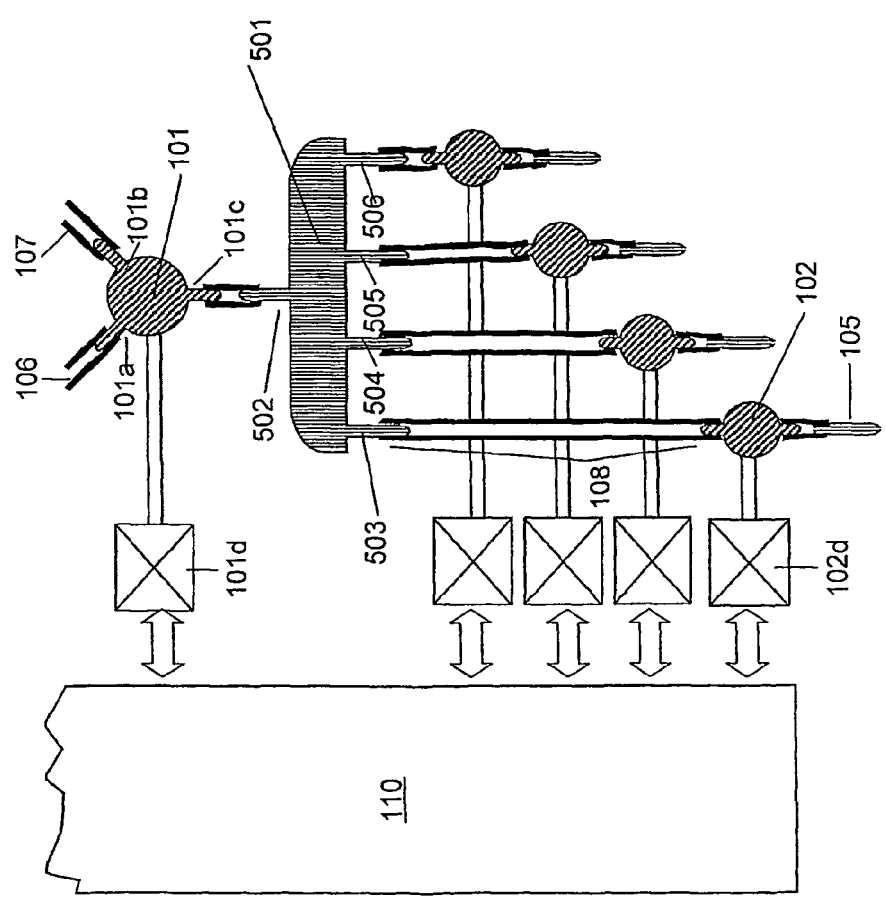
FIG. 5 is a schematic diagram of a multi-channel apparatus for precision fluid dispensing according to an embodiment of the invention.

FIG. 5 illustrates an embodiment of the invention in which outlet 101c of the two-way, three-port valve 101 is connected to a plurality of microvalve/dispensing nozzle combinations via pressure dividing manifold 501. Each microvalve is shown with its individual actuator, all under control of controller 110. This embodiment is useful for simultaneously aspirating and subsequently dispensing multiple samples (as an example, a four dispensing nozzle embodiment is shown in FIG. 5). Because each dispensing nozzle has its own, unique microvalve, the volume quantities can be independently adjusted for each dispensing nozzle by controlling the time that an associated microvalve is open. This can be used to fine tune sample volumes to equalize dispensing disparities resulting from non-idealities in the system, and/or it can be used to simultaneously dispense different sample volumes deliberately.

Variations and extensions of the embodiments described are apparent to one of ordinary skill in the art. For example, in reference to FIG. 1, nozzle 105 could be replaced with a pressure splitting manifold coupled to a plurality of combinations of microvalve and nozzle, for simultaneously dispensing a plurality of samples. Also, embodiments of the invention can be used to precisely dispense volumes of sample fluid for applications other than microarrays for biological and/or chemical testing. Other applications, features, and advantages of this invention will be apparent to one of ordinary skill in the art who studies this invention disclosure. Therefore the scope of this invention is to be limited only by the following claims.

The invention claimed is:
1. An apparatus for dispensing fluids comprising;
   multiple dispensing nozzles;
   multiple microvalves coupled to the dispensing nozzles;
   a two-way, three-port valve having first, second, and third ports, wherein the first port is coupled to the microvalves;
   a pressure dividing manifold operably connected between the first port of the two-way, three-port valve and the microvalves to divide pressure among the microvalves;
   a pressure tuning module comprising a first pressure source coupled to the second port of the two-way, three-port valve; and
   a second pressure source coupled to the third port of the two-way, three-port valve.
2. The apparatus of claim 1, wherein the pressure tuning module is a syringe pump.
3. The apparatus of claim 1, wherein the second pressure source comprises one of (i) a compressor, (ii) a pressurized gas vessel, or (iii) a pressurized working fluid reservoir.
4. The apparatus of claim 1, wherein the first microvalve is operably connected to a first microvalve actuator, the two-way, three-port valve is operably connected to a two-way, three-port valve actuator, and the pressure tuning module is operably connected to a pressure tuning module actuator, and wherein the microvalve actuator, the two-way, three-port valve actuator, and the pressure tuning module actuator are all operably connected to a software programmable controller.
5. The apparatus of claim 4, wherein the dispensing nozzle and the microvalve are mounted on a Z-axis up-and-down slide of a robotic positioner.
6. The apparatus of claim 5 wherein the apparatus for dispensing fluids and the robotic positioner are under the control of a common software programmable controller.
7. The apparatus of claim 6 configured to operate under the software programmable controller to fabricate microarrays.

* * * * *

UNITED STATES PATENT AND TRADEMARK OFFICE
CERTIFICATE OF CORRECTION

| | | |
|---|---|---|
| PATENT NO. | : 8,597,592 B2 | Page 1 of 1 |
| APPLICATION NO. | : 11/991723 | |
| DATED | : December 3, 2013 | |
| INVENTOR(S) | : Wang et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1626 days.

Signed and Sealed this
Fifth Day of May, 2015

Michelle K. Lee
*Director of the United States Patent and Trademark Office*